United States Patent
Sharma et al.

(10) Patent No.: US 9,636,011 B2
(45) Date of Patent: May 2, 2017

(54) SYSTEMS AND METHODS FOR SPECTRALLY DISPERSED ILLUMINATION OPTICAL COHERENCE TOMOGRAPHY

(71) Applicant: Carl Zeiss Meditec, Inc., Dublin, CA (US)

(72) Inventors: Utkarsh Sharma, Dublin, CA (US); Tilman Schmoll, Dublin, CA (US); Xing Wei, Dublin, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 117 days.

(21) Appl. No.: 14/789,889

(22) Filed: Jul. 1, 2015

(65) Prior Publication Data

US 2016/0000320 A1    Jan. 7, 2016

Related U.S. Application Data

(60) Provisional application No. 62/020,556, filed on Jul. 3, 2014.

(51) Int. Cl.
*A61B 3/12* (2006.01)
*A61B 3/10* (2006.01)
*G01J 3/45* (2006.01)
*G01J 3/28* (2006.01)

(52) U.S. Cl.
CPC .......... *A61B 3/102* (2013.01); *G01J 3/2823* (2013.01); *G01J 3/45* (2013.01)

(58) Field of Classification Search
CPC .......... A61B 3/102; A61B 2090/3735; A61B 3/1025; A61B 3/12; A61B 3/1225; A61B 3/14; A61B 5/0068

USPC ........ 351/206, 246, 205, 200; 356/479, 451, 356/456

See application file for complete search history.

(56) References Cited

U.S. PATENT DOCUMENTS

| | | | |
|---|---|---|---|
| 7,391,520 B2 | 6/2008 | Zhou et al. |
| 8,319,974 B2 | 11/2012 | Knighton et al. |
| 8,427,654 B2 | 4/2013 | Horn et al. |
| 8,442,284 B2 | 5/2013 | Rogers et al. |
| 8,446,593 B1 | 5/2013 | Ellerbee et al. |
| 8,705,048 B2 | 4/2014 | Everett et al. |
| 2007/0081236 A1 | 4/2007 | Tearney et al. |

(Continued)

OTHER PUBLICATIONS

Blazkiewicz, et al., "Signal-To-Noise Ratio Study of Full-Field Fourier- Domain Optical Coherence Tomography", Applied Optics, vol. 44, No. 36, Dec. 20, 2005, pp. 7722-7729.

(Continued)

*Primary Examiner* — Hung Dang
(74) *Attorney, Agent, or Firm* — Morrison & Foerster LLP

(57) ABSTRACT

Systems and methods are presented for acquisition and processing of spectrally dispersed illumination optical coherence tomographic data. Light from a source is distributed spectrally on the sample, and each acquisition simultaneously provides partial spectral interference information from multiple locations in the sample. Thus for a given spatial point, a single observation will be of a partial spectrum A-scan. When multiple partial spectrum A-scan observations are made at the same point by shifting the spectrum of light on to the tissue, the point can be observed by the entire broadband spectrum of the light source, thereby making it possible to create a full axial resolution A-scan.

19 Claims, 8 Drawing Sheets

(56) References Cited

U.S. PATENT DOCUMENTS

| | | |
|---|---|---|
| 2007/0233396 A1 | 10/2007 | Tearney et al. |
| 2013/0100456 A1 | 4/2013 | Yu et al. |
| 2013/0215431 A1 | 8/2013 | Ellerbee et al. |
| 2013/0235344 A1* | 9/2013 | Buckland ............... A61B 3/102 351/206 |
| 2013/0301000 A1 | 11/2013 | Sharma et al. |

OTHER PUBLICATIONS

Bonin, et al., "In Vivo Fourier-Domain Full-Field OCT of the Human Retina with 1.5 Million A-lines/s", Optics Letters, vol. 35, No. 20, Oct. 12, 2010, pp. 3432-3434.

Choma, et al., "Sensitivity Advantage of Swept Source and Fourier Domain Optical Coherence Tomography", Optics Express, vol. 11, No. 18, Sep. 8, 2003, pp. 2183-2189.

Ellerbee, et al., "Interleaved Optical Coherence Tomography", Optics Express, vol. 21, No. 22, Nov. 4, 2013, pp. 26542-26556.

Fercher, et al., "Eye-Length Measurement by Interferometry With Partially Coherent Light", Optics Letters, Optical Society of America, vol. 13, No. 3, Mar. 1988, pp. 186-188.

Fercher, et al., "Measurement of Intraocular Distances by Backscattering Spectral Interferometry", Optics Communications, vol. 117, May 15, 1995, pp. 43-48.

Grajciar, et al., "Parallel Fourier Domain Optical Coherence Tomography for in Vivo Measurement of the Human Eye", Optics Express, vol. 13, No. 4, Feb. 21, 2005, pp. 1131-1137.

Gronle, et al., "Laterally Chromatically Dispersed, Spectrally Encoded Interferometer", Applied Optics, Optical Society of America, vol. 50, No. 23, Aug. 1, 2011, pp. 4574-4580.

Hiratsuka, Hajime et al., "Simultaneous Measurements of Three-Dimensional Reflectivity Distributions in Scattering Media Based on Optical Frequency-Domain Reflectometry", Optics letters, Optical Society of America, vol. 23, No. 18, Sep. 15, 1998, pp. 1420-1422.

Huang, et al., "Optical Coherence Tomography", Science, vol. 254, Nov. 22, 1991, pp. 1178-1181.

Klein, et al., "Joint Aperture Detection for Speckle Reduction and Increased Collection Efficiency in Ophthalmic Mhz Oct", Biomedical Optics Express, vol. 4, No. 41, Mar. 28, 2013, pp. 619-634.

Lee, et al., "Line-Field Optical Coherence Tomography Using Frequency-Sweeping Source", IEEE Journal of Selected Topics in Quantum Electronics, vol. 14, No. 1, Jan./Feb. 2008, pp. 50-55.

Leitgeb, et al., "Performance of Fourier Domain vs. Time Domain Optical Coherence Tomography", Optics Express vol. 11, No. 8, Apr. 21, 2003, pp. 889-894.

Liu, et al., "Spectrally Encoded Extended Source Optical Coherence Tomography", Optics Letters, Optical Society of America, vol. 39, No. 24, Dec. 15, 2014, pp. 6803-6806.

Mohamed, et al., "Ultra Wide Wavelength Multiplexing/ Demultiplexing Conventional Arrayed Waveguide Grating (AWG) Devices for Multi Band Applications", International Journal of Emerging Technology and Advanced Engineering, vol. 2, No. 1, Jan. 2012, pp. 20-31.

Mujat, et al., "Swept-Source Parallel OCT", Optical Coherence Tomography and Coherence Domain Optical Methods in Biomedicine XIII, Proc. of SPIE, vol. 7168, 2009, pp. 71681E-1-71681E-8.

Nakamura, et al., "High-Speed Three-Dimensional Human Retinal Imaging by Line-Field Spectral Domain Optical Coherence Tomography", Optics Express, vol. 15, No. 12, Jun. 11, 2007, pp. 7103-7116.

Nankivil, et al., "Coherence Revival Multiplexed, Buffered Swept Source Optical Coherence Tomography: 400 Khz Imaging With a 100 Khz Source", Optics Letters, Optical Society of America, vol. 39, No. 13,, Jul. 1, 2014, pp. 3740-3743.

Peroz, et al., "Multiband Wavelength Demultiplexer Based on Digital Planar Holography for On-Chip Spectroscopy Applications", Optics Letters, Optical Society of America, vol. 37, No. 4, Feb. 15, 2012, pp. 695-697.

Potsaid, et al., "Ultrahigh Speed 1050nm Swept Source / Fourier Domain OCT Retinal and Anterior Segment Imaging at 100,000 to 400,000 Axial Scans per Second", Optics Express, vol. 18, No. 19, Sep. 13, 2010, pp. 20029-20048.

Povazay, et al., "Full-Field Time-Encoded Frequency-Domain Optical Coherence Tomography", Optics Express, vol. 14, No. 17, Aug. 21, 2006, pp. 7661-7669.

Tearney, et al., "Spectrally Encoded Confocal Microscopy", Optics Letters, Optical Society of America, vol. 23, No. 15, Aug. 1, 1998, pp. 1152-1154.

Tearney, et al., "Spectrally Encoded Miniature Endoscopy", Optics Letters, Optical Society of America, vol. 27, No. 6, Mar. 15, 2002, pp. 412-414.

Wieser, et al., "Multi-Megahertz OCT: High quality 3D imaging at 20 million A-scans and 4.5 GVoxels per second", Optics Express, vol. 18, No. 14, Jul. 5, 2010, pp. 14685-14704.

Wolf, Emil, "Three-Dimensional Structure Determination of Semi-Transparent Objects from Holographic Data", Optics Communications, vol. 1, No. 4, Sep./Oct. 1969, pp. 153-156.

Yelin, et al., "Spectral-Domain Spectrally-Encoded Endoscopy", Optics Express, vol. 15, No. 5, Mar. 5, 2007, pp. 2432-2444.

Yelin, et al., "Three-Dimensional Spectrally Encoded Imaging", Optics Letters, Optical Society of America, vol. 28, No. 23,, Dec. 1, 2003, pp. 2321-2323.

Yelin, et al., "Volumetric Sub-Surface Imaging Using Spectrally Encoded Endoscopy", Optics Express, vol. 16, No. 3, Feb. 4, 2008, pp. 1748-1757.

Zhou, et al., "Space-Division Multiplexing Optical Coherence Tomography", Optics Express, vol. 21, No. 16, Aug. 12, 2013, pp. 19219-19227.

Zuluaga, et al., "Spatially Resolved Spectral Interferometry for Determination of Subsurface Structure", Optics Letters, vol. 24, No. 8, Apr. 15, 1999, pp. 519-521.

\* cited by examiner

SYSTEMS AND METHODS FOR SPECTRALLY DISPERSED ILLUMINATION OPTICAL COHERENCE TOMOGRAPHY

PRIORITY

The present application claims priority to U.S. Provisional Application Ser. No. 62/020,556 filed Jul. 3, 2014 the contents of which are hereby incorporated by reference.

TECHNICAL FIELD

The present application relates to the field of optical coherence tomography. In particular, the present application describes embodiments related to producing and processing partial spectrum A-scans with optical coherence tomographic instrumentation.

BACKGROUND

Optical Coherence Tomography (OCT) is an interferometric technique that can provide images of samples including tissue structure on the micrometer scale in situ and in real time (Huang, D. et al., Science 254, 1178-81, 1991). OCT is based on the principle of low coherence interferometry (LCI) and determines the scattering profile of a sample along the OCT beam by detecting the interference of light reflected from a sample and a reference beam (Fercher, A. F. et al., Opt. Lett. 13, 186, 1988). Each scattering profile in the depth direction (z) is reconstructed individually into an axial scan, or A-scan. Cross-sectional images (B-scans), and by extension 3D volumes, are built up from many A-scans, with the OCT beam moved to a set of transverse (x and y) locations on the sample.

Many variants of OCT have been developed where different combinations of light sources, scanning configurations, and detection schemes are employed. In time domain OCT (TD-OCT), the pathlength between light returning from the sample and reference light is translated longitudinally in time to recover the depth information in the sample as illustrated in FIG. 1. FIG. 1 shows a prior art TD-OCT system with a moving reference mirror 103. Also shown is a depiction of the type of data that is produced: 101 showing an A-scan, and 102 showing a 2D B-scan (composed of multiple A-scans).

In frequency-domain or Fourier-domain OCT (FD-OCT), a method based on diffraction tomography (Wolf, E., Opt. Commun. 1, 153-156, 1969), the broadband interference between reflected sample light and reference light is acquired in the spectral frequency domain and a Fourier transform is used to recover the depth information (see for example Fercher, A. F. et al., Opt. Commun. 117, 43-48, 1995). The sensitivity advantage of FD-OCT over TD-OCT is well established (see for example Leitgeb, R. et al., Opt. Express 11, 889, 2003; Choma, M. et al., Opt. Express 11, 2183-9, 2003).

There are two common approaches to FD-OCT. One is spectral domain OCT (SD-OCT) where the interfering light is spectrally dispersed prior to detection and the full depth information can be recovered from a single exposure as illustrated in FIG. 2. In FIG. 2, an SD-OCT system is depicted along with the type of data that is produced, first as a spectrally dispersed interferogram 201, an then how it looks after being Fourier-transformed 202. A B-scan image 203 produced by combining several A-scans is also depicted. In an SD-OCT system as illustrated in FIG. 2, light from a broadband light source 206 is split by a coupler 210 into reference and sample arms. The reference arm light travels towards a stationary reference mirror 205 where it is back reflected and returns along the same path to coupler 210. Light in the sample arm is directed towards an eye 209 of a patient by a series of optical elements. The light can be scanned over a plurality of transverse locations on the eye using a scanner 208. The back-reflected light from the tissues of the eye 209 is then collected and interfered with the light of the reference arm at coupler 210 and the interfering light is spectrally dispersed by a grating 207 onto a detector array 204. The electrical signals from the detector are transferred to a processor where the spectral interferogram is transformed into A-scans and then combined to create B-scans of the eye. The sample and reference arms in the interferometer could consist of bulk-optics, photonic integrated circuits, fiber-optics or hybrid bulk-optic systems and could have different architectures such as Michelson, Mach-Zehnder or common-path based designs as would be known by those skilled in the art. The processing could be accomplished in the data collection instrument or remote from the instrument. Parallel processing techniques could be employed to expedite processing.

The second common type of FD-OCT is swept-source OCT (SS-OCT) where the broadband source is replaced with a frequency tunable source that is swept over a range of optical frequencies in rapid cycles and the resulting signal is detected in time using for example, a balanced detector, therefore encoding the spectral information in time. In traditional point scanning or flying spot techniques, a single point of light is scanned across the sample. These techniques have found great use in the field of ophthalmology. However, current point scanning systems for use in ophthalmology illuminate the eye with less than 10% of the maximum total power possible for eye illumination spread over a larger area. It may not be immediately possible to significantly increase the illumination power with the current point-scanning architectures since the systems already operate close to their maximum permissible exposure for a stationary beam. Parallel OCT techniques, which spread the illumination light over a larger area on the tissue may be able to overcome this challenge. Further, the typically higher acquisition speed of such parallel systems will result in comprehensively sampled volumes which are required for applying computational imaging techniques.

In parallel techniques, a series of spots (multi-beam), a line of light (line-field), or a two-dimensional field of light (partial-field and full-field) is directed to the sample. The resulting reflected light is combined with reference light and detected. Parallel techniques can be accomplished in TD-OCT, SD-OCT or SS-OCT configurations. A number of groups have reported on different parallel FD-OCT configurations (see for example Hiratsuka, H. et al., Opt. Lett. 23, 1420, 1998; Zuluaga, A. F. et al., Opt. Lett. 24, 519-521, 1999; Grajciar, B. et al., Opt. Express 13, 1131, 2005; Blazkiewicz, P. et al., Appl. Opt. 44, 7722, 2005; Považay, B. et al., Opt. Express 14, 7661, 2006; Nakamura, Y. et al., Opt. Express 15, 7103, 2007; Lee, S.-W. et al., IEEE J. Sel. Topics Quantum Electron. 14, 50-55, 2008; Mujat, M. et al., Optical Coherence Tomography and Coherence Domain Optical Methods in Biomedicine XIII 7168, 71681E, 2009; Bonin, T. et al., Opt. Lett. 35, 3432-4, 2010; Wieser, W. et al., Opt. Express 18, 14685-704, 2010; Potsaid, B. et al., Opt. Express 18, 20029-48, 2010; Klein, T. et al., Biomed. Opt. Express 4, 619-34, 2013; Nankivil, D. et al., Opt. Lett. 39, 3740-3, 2014).

Non-confocal parallel OCT methods, especially full-field OCT systems can suffer from image degradation due to the increased collection of multiply scattered light. When imaging highly scattering samples, as for example the retinal pigment epithelium (RPE) in the eye, it is beneficial to suppress multiple scattered light and therefore enable imaging of deeper structures within the sample (e.g. the choroid and sclera in the case where the human eye is the sample).

Multi-beam OCT systems as well as joint aperture OCT systems have complicated system architecture with multiple interferometers. Both space-division multiplexing OCT (Zhou et al., Opt Exp 21, 19219, 2013) and interleaved OCT (Ellerbee et al., Opt Exp 21, 26542, 2013) utilized the concept of translating the long coherence length of the source into high OCT imaging speed. Different illuminated points on the sample had different optical path lengths and the interferometric signal from each point was extracted from a different imaging depth. However, one of the critical limitations of space-division multiplexing is to separate desired signal from unwanted reflections at the optical surfaces or tissue. For example, thick samples (such as signal from vitreous) may cause overlap with imaging windows of other channels and result in artifacts. In addition, both the systems use complex sample arm designs to illuminate multiple locations in the sample (by using either splitters or virtually imaged phased arrays—VIPA) that lead to around ~10 dB losses in the sample arm. Ellerbee et al. (2013) teach illuminating multiple points on the sample in their technique of interleaved OCT (Ellerbee et al. US Patent Publication No. 20130215431). In their technique, roughly the full spectral width of the source is divided into P sets of unique spectrally interleaved wavelength components. Each point is illuminated by roughly the full spectral width of the source. While this allows the benefits of being able to use more power to illuminate the sample safely, the mechanisms to de-multiplex the light at the sample and detection ends add significant complexity and losses in the system.

Spectral encoded endoscopy spectrally spreads the light on to a sample (see for example Yelin et al., Opt Lett 28, 2321, 2003 and Yelin et al., Opt Exp 15, 2432, 2007 and Tearney et al., Opt Lett 23, 1152, 1998 and Tearney et al., Opt Lett 27, 412, 2002). However, this approach has significantly poorer axial resolution as only a partial spectral window is used from the available full spectral width of the source for A-scan reconstruction. Gronle et al. also demonstrated a method to spectrally disperse the light on the sample and used it for height profile measurement of the sample (Gronle et al., App Opt 50, 4574, 2011). However, this approach also compromises on the axial resolution as it does not utilize the full spectral bandwidth.

SUMMARY

Parallel OCT provides a solution for obtaining high-speed OCT data without sacrificing sensitivity as more power can be used to illuminate the tissue safely. In the embodiments of the present application describing spectrally dispersed illumination OCT, broadband light from the source is distributed in the form of a spectrum onto the sample, and each acquisition simultaneously provides spectral interference information from multiple locations in the sample. However, each location is illuminated only with the partial bandwidth of the source at each instance in time. A scanner can follow the direction of the spectrum on the sample to generate subsequent acquisitions that can be used to obtain the complete spectral interference information (i.e. the complete spectral bandwidth of the source) or a subset thereof at each spatial location in the sample. Effectively, as the spectrum moves along its own direction, each location is sampled by the complete spectrum of the broadband source; thereby achieving full axial resolution when the partial spectrum data is combined in post-processing to yield a combined A-scan. Both spectral domain and swept-source embodiments are possible. This method has the advantage of line field OCT, to be able to illuminate multiple locations in the tissue simultaneously, while still being able to maintain high confocality, minimizing the image degradation effects of multiple scattering. The confocality of the spectrally dispersed illumination OCT system, i.e. the ability to reject out of focus light, is maintained, because the sample light can be coupled into a single mode fiber, which would serve as a pinhole. This is in general not possible with other non-confocal parallel techniques, such as full field OCT. Despite their confocality, spectrally dispersed illumination OCT systems can operate at higher illumination powers, because dispersing the light onto a larger area on the sample increases the total maximum permissible exposure.

DETAILED DESCRIPTION

A basic concept of the present application is to spectrally disperse or de-multiplex illumination of the incident light at the sample, move the spectrally dispersed light along the spatial direction of dispersion and spectrally resolve the detection of the light interference. The broadband light from the source is distributed spectrally on the sample, and each acquisition simultaneously provides partial spectral interference information from multiple locations in the sample. Thus for a given spatial point, a single observation will be of a partial spectrum A-scan. When multiple partial spectrum A-scan observations are made at the same point by shifting the spectrum of light on to the tissue, the point will be illuminated by the entire broadband spectrum of the light source over time, thereby making it possible to construct a full axial resolution A-scan.

Spectral spreading of the incident beam on a sample makes it possible to increase incident power within safe limits. Hence it could provide the same advantages as line-field OCT systems in terms of increased incident safe power. Unlike multi-beam OCT systems, the embodiments described herein do not necessarily require multiple interferometers. In addition, spectrally dispersed illumination of the sample ensures that the performance of rejection of the multiple scattering signal is similar to that of point-scanning systems. Confocality, i.e., the ability to reject out of focus light, is maintained, because the light in the path from the sample to the detector is, in contrast to other parallel systems, for example full-field OCT, can be coupled into a single mode fiber, which serves as a pin hole.

Figure 1:
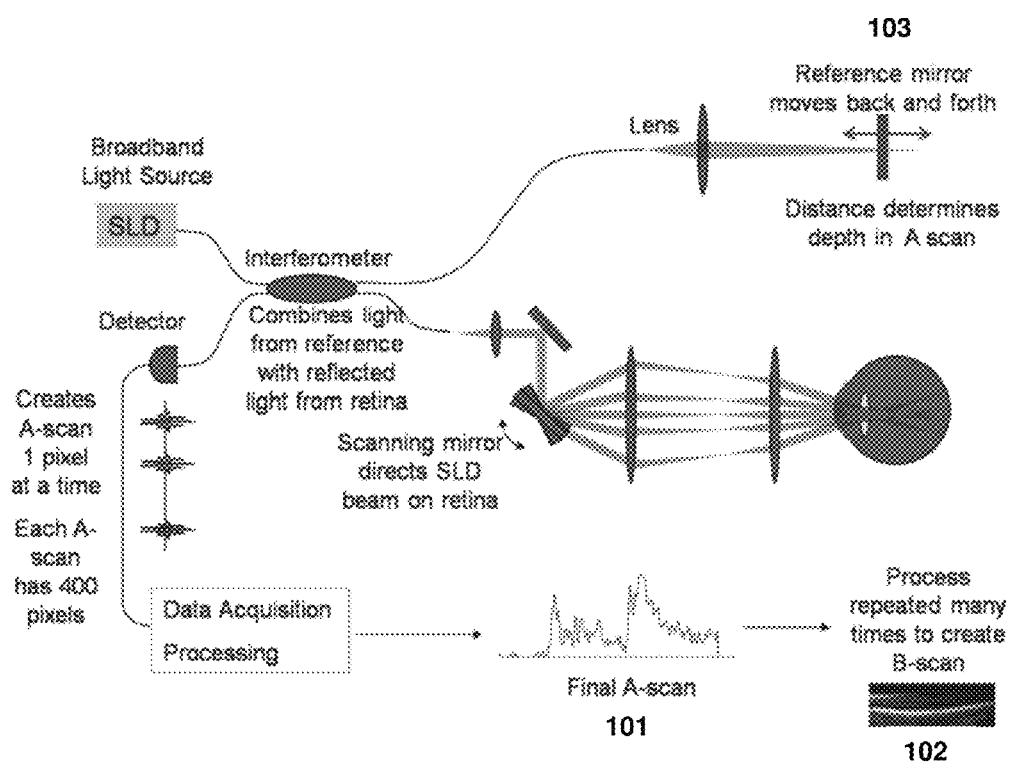
FIG. 1 is a schematic of a generalized prior art TD-OCT system.
Figure 2:
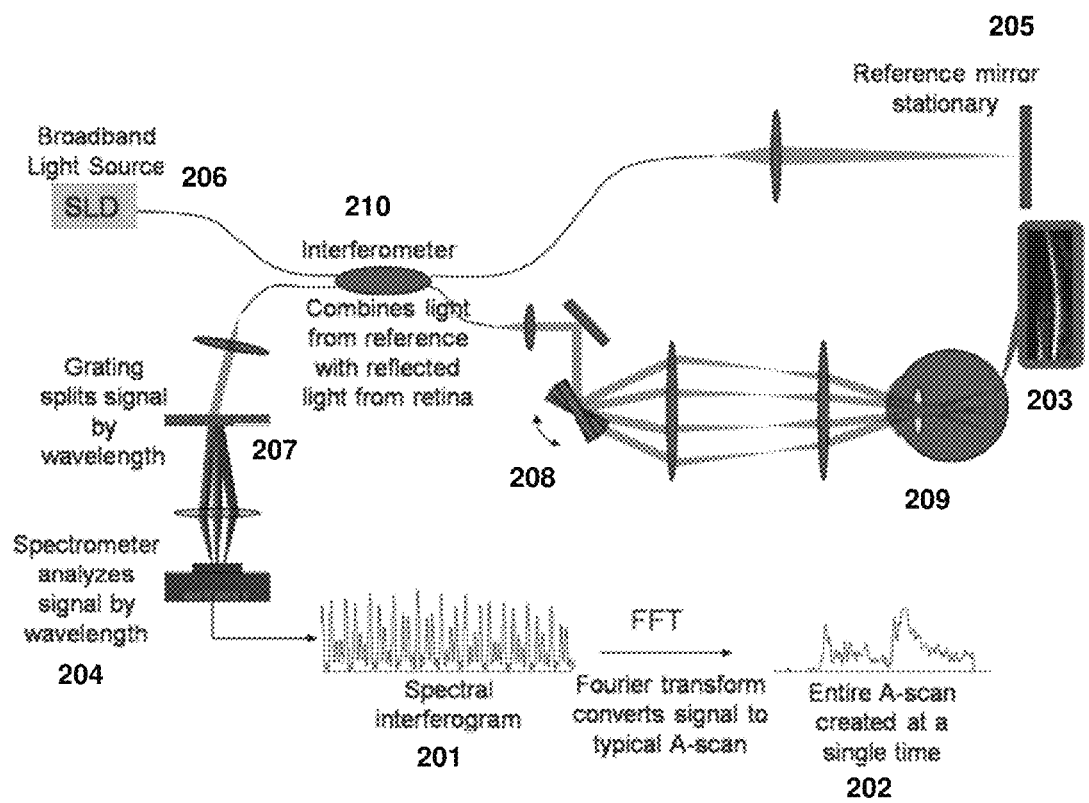
FIG. 2 is a schematic of a generalized prior art SD-OCT system.
Figure 3:
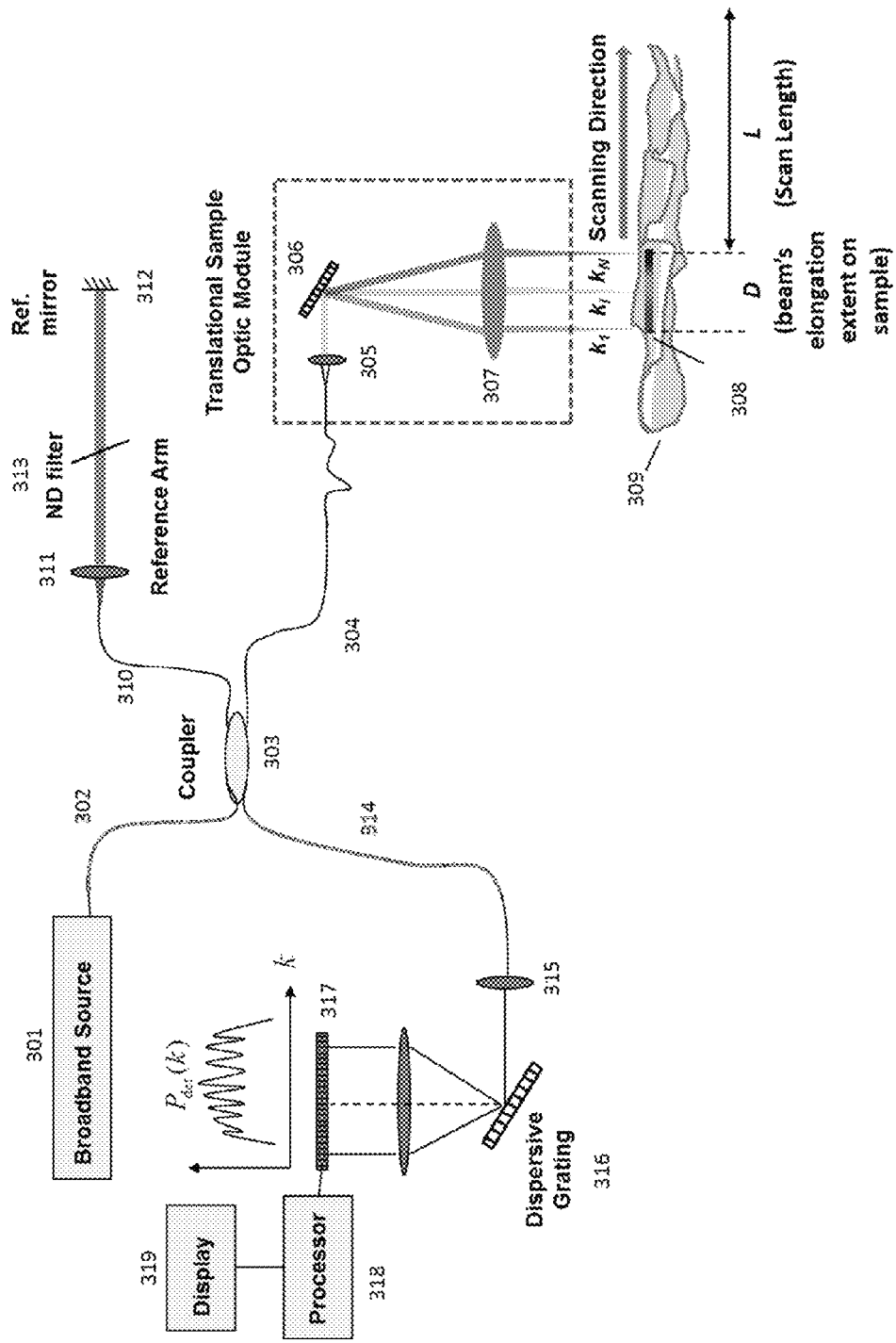
FIG. 3 illustrates an SD-OCT embodiment of a Spectrally Dispersed Illumination OCT System in accordance with the subject invention.

A generalized illustration of an SD-OCT based spectrally dispersed illumination OCT system according to this concept is illustrated in FIG. 3. Light from a broadband source 301, a typical source being a superluminescent diode (SLD), is coupled into single-mode fiber 302 and then routed to a splitter, in this case fiber coupler 303 which divides the light into sample and reference paths. Light in the reference path travels through fiber 310 and is collimated by lens 311 at the output of the fiber. The collimated light travels towards a stationary mirror 312 where it is back reflected. The back reflected light returns along the same path, traveling the same overall distance as the light in the sample path when it arrives on its return path at coupler 303. A neutral density filter 313 can be used to adjust the intensity of the light in the reference arm to optimize the collected signal. Light in the sample path travels through fiber 304 and is collimated by lens 305 at the output end of the fiber. The collimated light is directed to a spectrally dispersing optical element 306, such as a prism or grating, or multiband demultiplexer (MDMX). The light is then spectrally dispersed into a spectrum and leaves the spectral dispersing optic at angles relative to it that are dependent upon the wavelength. The spectrum is then collimated by an optic 307, a lens or mirror, and the dispersed wavelengths 308 are optically directed to a sample 309, a typical sample being tissues in the human eye. Illumination by the spectrum has an increased or elongated spread on the sample (D) compared to non-dispersed illumination that may allow increased sample power within the safety regulations. The light back reflected or scattered from the sample at each illumination location travels back along the illumination path and is spectrally recombined by optical element 306. The spectrally combined light is launched back into fiber 304 insuring confocal detection. The sample light is combined with back reflected reference light at coupler 303 where they coherently interfere. The combined light travels through fiber 314 and is collimated by optic 315 at the end of the fiber. The collimated light is spectrally dispersed, in this case by grating 316 and imaged onto detector array 317 which detects the combined light and generates signals in response thereto. The electrical signals from the detector array are transferred to the processor 318 where the detected wavelengths are mapped to illumination locations on the sample. The processor is shown as a single entity, but may contain for example a central processing unit (CPU), a field-programmable gate array (FPGA), a digital signal processor (DSP), an application specific integrated circuit (ASIC), a graphic processing unit (GPU), a system on chip (SoC) or a combination thereof, which performs some, or the entire signal processing steps, prior to passing the data on to the host processor. The processor is operably attached to a display 319 for displaying images of the data. The interferometer could consist of bulk-optics, photonic integrated circuits, fiber-optics or hybrid bulk-optic systems and could have different architectures such as Michelson, Mach-Zehnder or common-path based designs as would be known by those skilled in the art. The system has minimum cross-talk between adjacent locations in the sample (due to confocality) as the illumination as well as detection is spectrally dispersed.

Scanning of the dispersed light or spectrum to cover a larger area on the sample may be accomplished along the elongation direction of the spectrum on the sample or another direction. The scanning mechanism shown in FIG. 3 is of the translational kind where the scanning motion is linear along the direction of spectral dispersion or elongation. There are a variety of ways to accomplish the sweeping or translating of the spectrum across the tissue to form the B-scan. A common approach, especially in OCT, is to use moveable mirrors, such as galvanometer based scanners to sweep the spectrum. Normally two galvanometer based scanners would be required, one for each of the two spatial dimensions. An alternative approach would be to have the dispersing element and its fore- and after-optical components on a translatable stage. The stage could be movable in either one or two dimensions, with perhaps one of the dimensional movements being provided by moveable mirrors. One embodiment would be a combination of a single galvanometer scanner and a translatable stage.

The embodiment of FIG. 3 consists of spectrally dispersing light onto tissue, collecting OCT partial spectrum A-scan signals at lateral points of the sample along that spectrum, offsetting or scanning the spectrum in a lateral dimension, and then obtaining another set of partial spectrum A-scans. This process can be repeated until all desired lateral points on the tissue have been observed, as is embodied in the schematic of FIG. 7. The horizontal axis in FIG. 7 indicates the scan direction on the sample. The vertical axis indicates time or successive detector acquisition.

The horizontal shifting of the line indicates that the elongated beam is moving along the scan direction. It can be seen from the figure that each spectral acquisition at a given time contains partial spectral information from multiple spatial locations. Hence if contiguous spectral bins from successive detector acquisitions are combined appropriately in a post-processing reconstruction, then spectral interference signal over the entire source bandwidth can be obtained from a given sample location. Effectively a mapping between wavenumber and spatial location on the sample is created.

The spectrally dispersing element can be any one of the group comprising: reflection gratings, transmission gratings, transmission prisms, reflection prisms, grisms, spectrally dispersing fibers, and multiband de-multiplexer (see for example Peroz et al., Opt Lett 37, 695, 2012 and Mohamed et al., Int J Emerg Tech & Adv Eng 2, 20, 2012, hereby incorporated by reference). Another optical component that would produce multiple spectra would be a cross-disperser, e.g., prism or grating, placed after or before the first dispersing element, a grating, for example. This would separate out the orders and provide additional wavelength and spatial coverage on the tissue. The spectral quality of the light impinging on a lateral point will depend upon the lateral size of that point, the characteristics of the focusing optic (camera or objective lens), and the nature of the spectrally dispersing element, and of course, on the spectral content of the light source.

As an illustration, it is assumed that the spread of the spectrum on the tissue is limited by wavelengths $\lambda_1$ at the short wavelength end, and at the long end of the wavelength spectrum. An alternative nomenclature is to use wavenumbers, such as $k_1$ and $k_N$ as depicted in FIG. 3. An intermediate wavenumber between these two extrema is designated as $k_i$. It must be noted that in this embodiment, the spectrum illuminates a plurality of spatial locations on a sample such that each location on the sample is interrogated by a given wavelength band (or packet or partial spectrum or subspectrum) that is smaller than the full spectral width of the source or of the spectrum. If the illuminated line on the sample could be divided into N spatial locations, then effectively we are dividing the full spectral range of the source into N wavelength bands (or packets or subspectra) such that the wavelength bands (or packets) are largely contiguous and each wavelength band has a different central wavelength.

While the spectrum herein is described as being a finite length, in practice there will be a fall-off at either extremum due to a diminishing efficiency of a grating (off blaze), for example, or any other commonly known spectrally dispersive optical components. Should this be a problem or if a modified spectral shape with respect to dispersion angle is desired, a bandpass filter or spatially/spectrally varying transmission element, preferably with a desired transmission profile could be inserted just after the spectrally dispersive optical component. This will provide the desired distribution of light intensity of the dispersed light projected onto the tissue.

Any source of broadband light commonly used in OCT can be used for the embodiments presented herein. SLDs, lasers, swept source lasers, which typically have a central wavelength around 850 nm with a 50 nm or more spectral bandwidth. Alternatively, or even in addition to this standard wavelength, are the use of lasers producing light at 1.05 μm or any other wavelength for that matter that may be desirable for investigating a particular sample.

Such a combination of multiple wavelengths could be used together, for example in an embodiment of a dual or N—light system, where an optical train downstream of the light sources produces spectra that are, for example, adjacent to one another, or overlapping, thus producing a dual color system capable of imaging tissues of different depths. For example, 850 nm is typically used for the retinal layers, while 1.05 μm is used to reach down below the retina into the choroid, and 1.3 μm is also used to obtain greater penetration depth for anterior segment imaging of the eye. Light of any useful wavelength range can be used in the basic embodiment. Overlapping spectra at the tissue can be later separated by a dichroic located subsequent to back-reflection from the tissue. Multiple spectra may be arranged in any convenient manner such as adjacent or even overlapping or collinearly arranged.

In an SS-OCT implementation of the embodiment, the SLD shown in FIG. 3 is replaced with a frequency tunable source such as an external cavity tunable laser (ECTL) or a sampled grating distributed Bragg reflector laser (SG-DBR), and the dispersive grating and array detector are replaced with a balanced photodiode detector in order to acquire the spectral information as a function of time. In the SS-OCT embodiment, the light would be scanned as it was tuned resulting in partial spectrum A-scans being acquired at different transverse locations on the sample. The reconstruction would be analogous to the SD-OCT case. The interfering reference and sample light can, as in the SD-OCT case be detected with a spectrometer, which may contain an array of photodiodes, such as that available in area (2D, e.g., CCD or CMOS) or linescan cameras would also suffice. The latter would be appropriate if multiple sources of light (V in number, the multiplex factor) produced what would be in effect a line, or as commonly known in the art of spectroscopy, an effective or virtual longslit (extended illumination in the direction orthogonal to the dispersion direction). With sufficient spatial coverage allowed by this approach, the reduction in total time to image the retina would be reduced by $(V)^{-1}$. Alternatively the spectrometer can be replaced by a point detector such as for example a single photodiode or a balanced detector. In that case the spectral information is captured purely as a function of time.

There are several key parameters that will impact the A-scan reconstruction algorithm. These parameters are:
1. D: Illumination line size on the sample, along the axis of elongation
2. L: Scan length or the distance traversed by the center of the line on the sample.
3. $W_0$: Beam spot size for a given wavelength.
4. ΔX: Pixel spacing or the distance traversed by the center of the line on the sample between two successive detector acquisitions.
5. τ: Exposure time for each spectral acquisition.

It must be noted that the above parameters play a critical role in the system performance. The ratio of the illumination line size and the scan length will determine the effective use of sample power for signal generation as the spatial locations at either ends are only illuminated by partial source bandwidth. In order to acquire the full spectral information for scan length L, the illumination center needs to move physically by a total distance of L+D. For example, if the line spread size (D) is 0.5 mm, and the scan length is 6 mm, then the effective duty cycle of full-axial resolution A-scan acquisition would be 6/(6+0.5)~92%. A 0.5 mm spread on the sample is still sufficiently large to increase the power on the sample manifolds.

Assuming the spectral frequency ($k=2\pi/\lambda$) spreads linearly across distance D, we can divide the full spectrum into D/ΔX equally spaced spectral sections (bands), each corresponding to one lateral sample location. In the subsequent acquisition, the spectral section of a given sample location shifts to the neighboring section. Over a total number of D/ΔX acquisitions, the full spectrum of a given sample location can be obtained by combining or stitching together the spectral sections from all these acquisitions. Standard normalization and interpolation methods will be used to ensure that the complete spectral A-scan reconstruction could be done without any artifacts.

Figure 4:
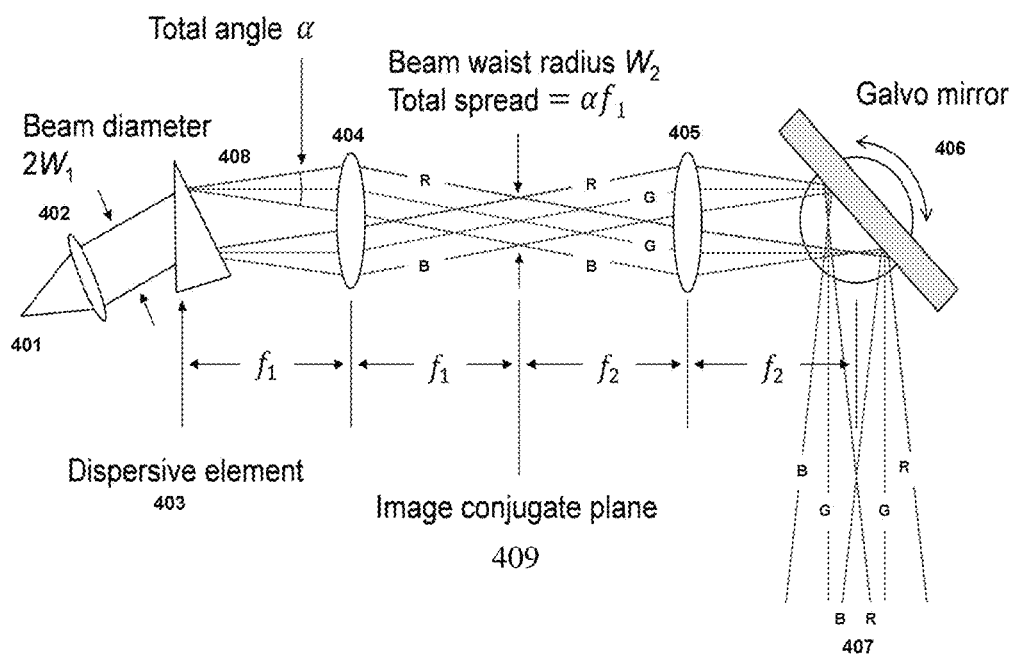
FIG. 4 is an optical layout of the sample arm to chromatically disperse the OCT beam in one embodiment of the invention (dimensions not to scale). Color rays of the spectra emerging from the dispersive element are denoted R for red, G for green, and B for blue.

In one embodiment of the present application, for which the optical layout of the sample arm is depicted in FIG. 4, the OCT beam 401 is collimated at optical element 402 with a beam diameter of $2W_1$ ($1/e^2$). The collimated OCT beam is sent through a dispersive element 403, which could be a prism or a grating. The dispersive element is imaged to the galvanometer mirror 406 (scanner) through two lenses of focal lengths $f_1$ (404) and $f_2$ (405), which are arranged as a telescope. The output beam 408 from the dispersive element 403 has a total angular spread of a for the entire optical spectral bandwidth of Δλ. At the image conjugate plane 409, the spatial spread is equal to $\alpha f_1$. The diffraction-limited beam waist radius at this conjugate plane is:

$$W_2 = \frac{\lambda f_1}{\pi W_1}$$

where λ is the center wavelength. The spread to waist ratio is then:

$$\frac{\text{Spread}}{W_2} = \frac{\alpha f_1}{\lambda f_1/(\pi W_1)} = \frac{\pi \alpha W_1}{\lambda}$$

Note this ratio is independent of focal length $f_1$, and it is entirely determined by the optics design of the dispersive element ($W_1$ and $\alpha$). This spectral spread to beam waist ratio is a key parameter and it is preserved through the imaging system. At the sample location, it is the ratio $D/W_0$ (or $D/\Delta X$ if $\Delta X \approx W_0$).

Figure 5:
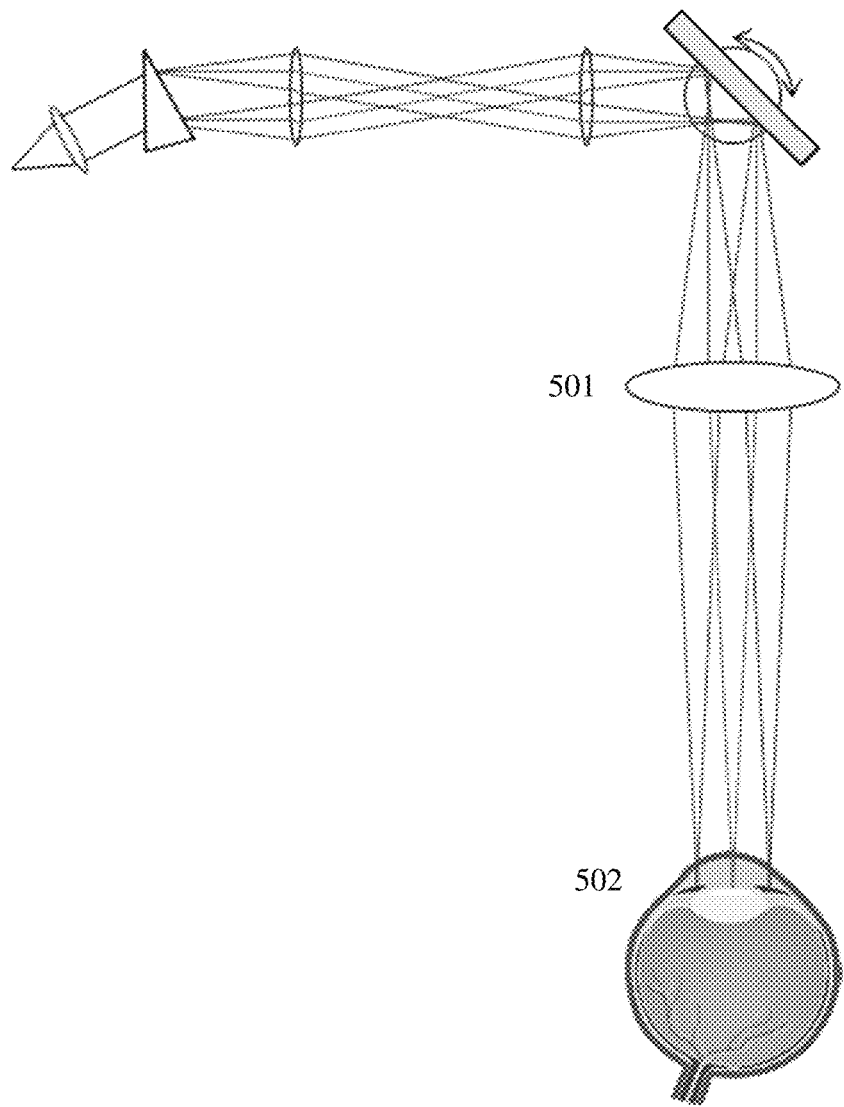
FIG. 5 is an optical layout to show spectrally dispersed illumination OCT for anterior segment imaging of the eye according to one embodiment of the invention (dimensions not to scale).
Figure 6:
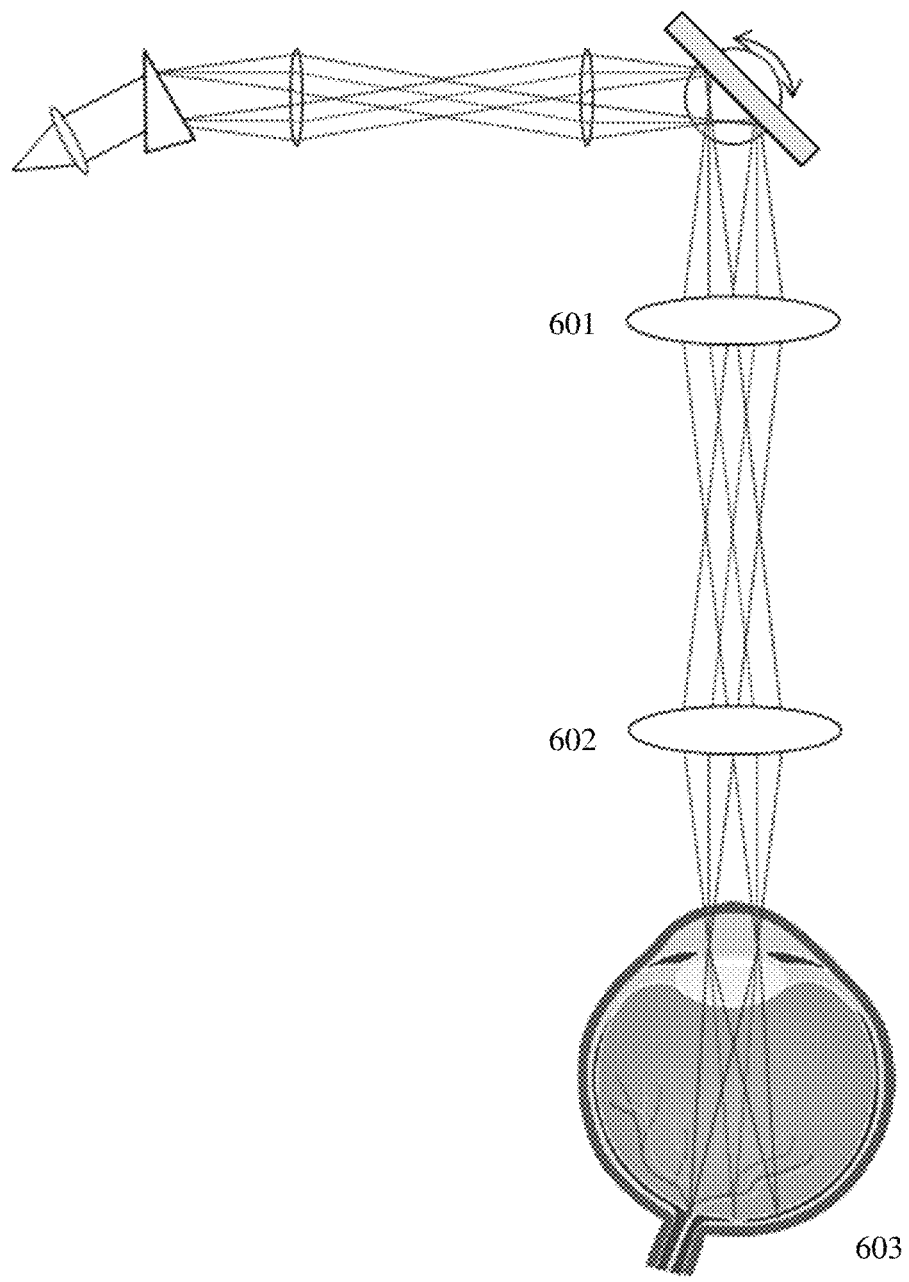
FIG. 6 is an optical layout to show spectrally dispersed illumination OCT for posterior segment imaging of the eye according to one embodiment of the invention (dimensions not to scale).

It must be noted that the optical layout shown in FIG. 4 can be used either for posterior or anterior segment imaging of the eye or other tissues. In one of the embodiments for the posterior eye scanning, the galvo mirror pivot point will be imaged to the pupil of the eye being scanned, by additional optical elements 407 downstream of the one or more galvanometers. FIGS. 5 and 6 show the embodiments to image anterior and posterior segment of the eye, respectively. In FIG. 5, the imaging optic 501 provides focus onto the front or anterior segment 502 of an eye. In FIG. 6, to reach the posterior segment, the retina, for example, requires two optical components, one 601 to produce a collimated beam and the other one 602 to focus the light onto the retina 603, for example. OCT systems can be configured with adjustable optical components to achieve both anterior and posterior imaging of the eye.

Interference fringes from multiple acquisitions will have multiple packets of wavelengths from the same lateral position. One could apply a spectral shaping as well as phase correction functions to the interference signals from these multiple packets of wavelengths before adding them up. After combining partial spectral interference fringes from multiple acquisitions, the remapped spectral interference signal for a given spatial point will span the complete bandwidth of the source to get the full resolution. After that another spectral shaping function could be applied to this remapped spectral interference signal prior to applying an inverse Fourier transform.

Upon assembling a set of partial spectrum A-scans for a given spatial point, these are then processed into a combined A-scan. This yields the highest axial resolution as compared with that obtainable by any one partial spectrum A-scan or even by processing any subset of the full set of partial spectrum A-scans available for that spatial point.

Figure 7:
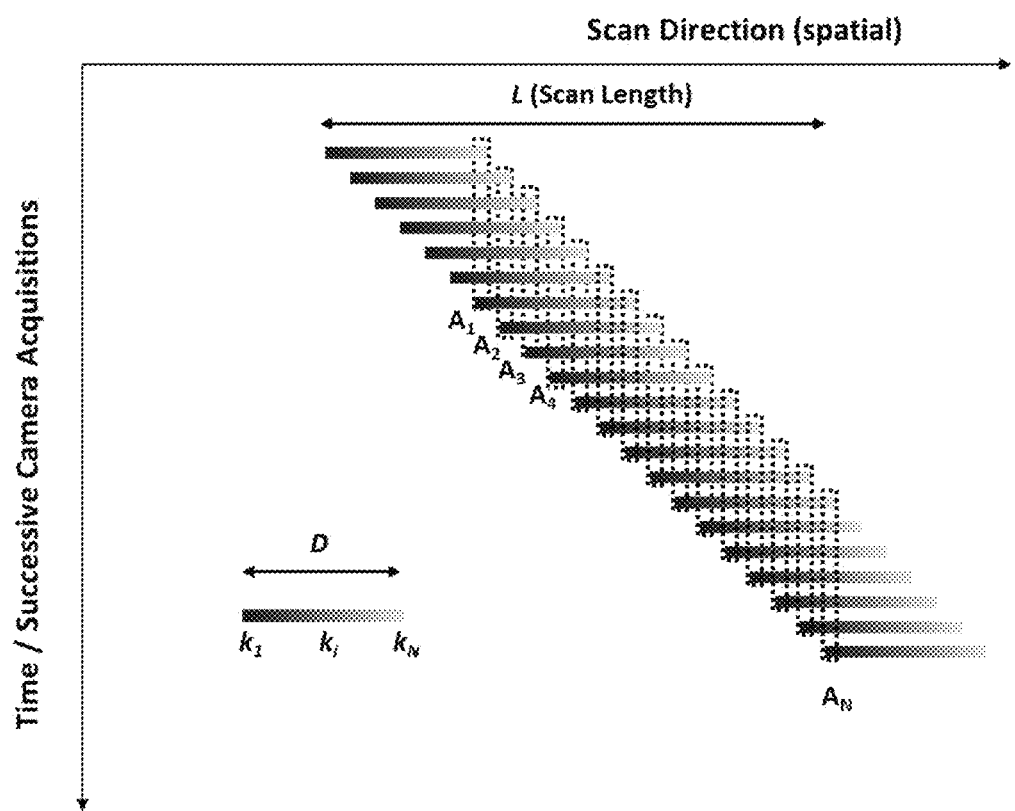
FIG. 7 is a schematic showing one embodiment to the reconstruction of a full-axial resolution A-scan based upon the methodology and apparatus as outlined in the present application.

An embodiment for combining the partial spectrum A-scan data into a high axial resolution volumetric dataset is straightforward and is depicted in FIG. 7. The totality of partial spectrum A-scans of a given lateral or spatial point are assembled and combined into a combined A-scan, thus forming the complete high axial resolution depth information in the z-dimension for that particular point. Thus if the lateral or spatial scan comprises a 2D dimension of I by J lateral points or pixels, then there will be a totality of I×J A-scans with the highest axial resolution possible, which can then be assembled into a single 3D volumetric dataset, or some subset thereof.

Given the complexity of the datasets that are generated with the aforementioned systems, the ability to organize and perform functional transformations to the data with a speed that provides at least near real-time visualization may require special processing power than what is available in a single central processing unit (CPU). Such computational devices such as graphics processing units (GPUs), digital signal processors (DSPs), field-programmable gate arrays (FPGAs), and any appropriate hardware accelerator/parallel processor for computation would be appropriate in this embodiment.

Figure 8:
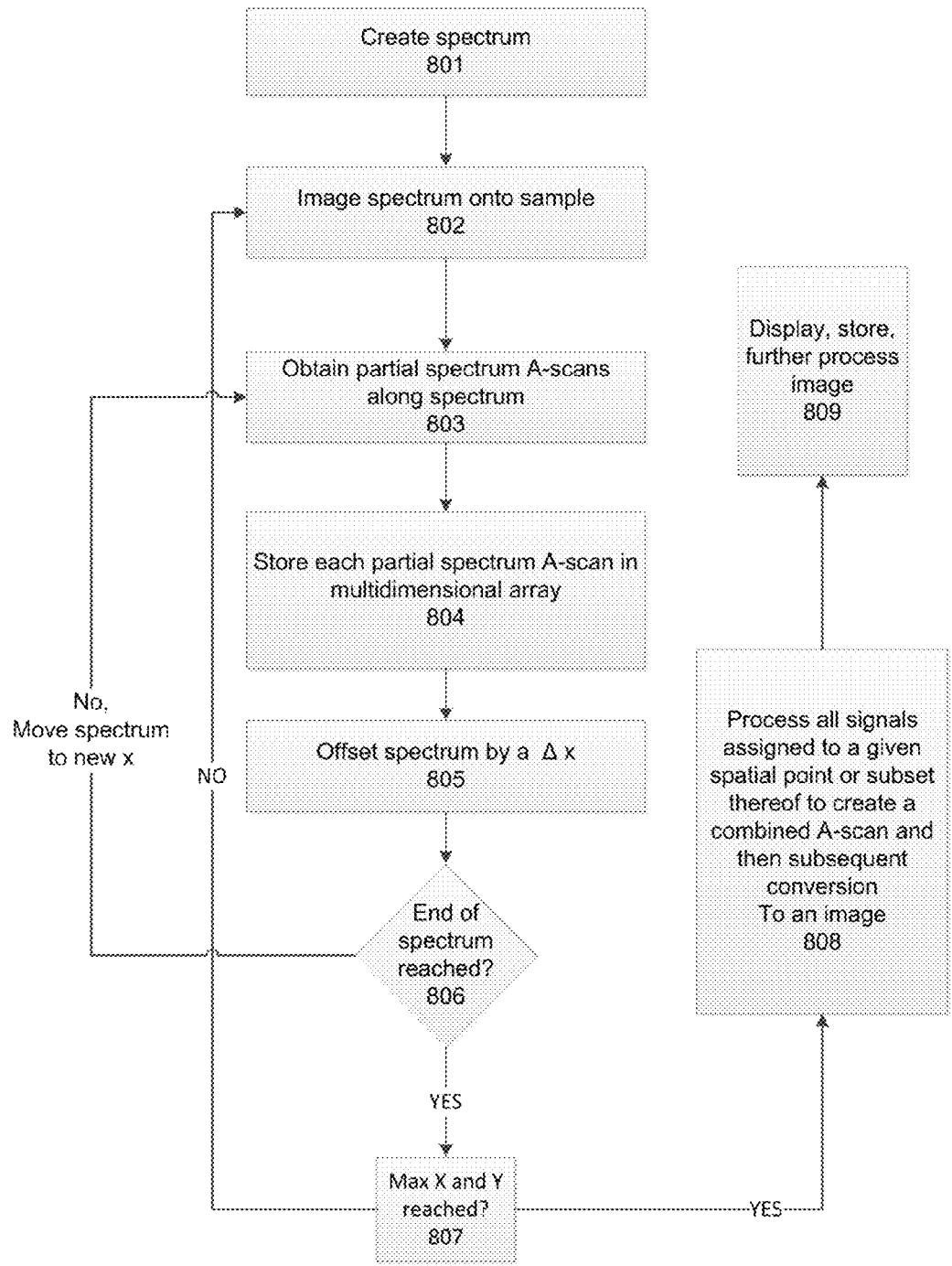
FIG. 8 is a flow chart of one embodiment for spectrally dispersed illumination OCT describing the steps in the acquisition of partial spectrum A-scans and their subsequent processing to achieve a combined A-scan.

The flow chart in FIG. 8 presents the steps of one embodiment of the present application. A spectrum of light is produced 801 and is then imaged onto a sample 802, at a given lateral location. Then a partial spectrum A-scan is obtained at each desired point along the spectrum 803 and the partial spectrum scans are stored in a multidimensional array 804, for later processing. The spectrum is then offset by an increment 805 along its spectral dimension (taken in this described embodiment to be designated x). If (806) the repositioning from 805 places the potential beam over a non-spectrum illuminated sample, then there is the option to perform additional partial spectrum scans over the sample by changing either x or y or both 803. When the maximum desired areal coverage of the sample has occurred (807), the multidimensional array can be processed as desired yielding an image 808, which can then be displayed, stored, or further processed 809. The multidimensional array can also be stored for later processing.

Another embodiment consists of inserting into the optical train downstream of the spectral disperser, a rotatable prism or other optical element or elements to rotate the spectrum onto the sample or tissue. This allows additional manipulation of the location of the spectrum onto the sample. Prisms that can rotate images are Amici Root, dove, half penta, Harting-Dove, Double Dove, Abbe, folded Abbe, Vee, Pechan, Raentsch, or Schmidt. Other optical components and mechanisms to rotate an image to a desired angle would be well known by the skilled person in the art.

Those skilled in the art can also adapt the embodiments of this invention for various OCT imaging applications and functional OCT such as OCT angiography, Doppler OCT, polarization-sensitive OCT, spectroscopic OCT etc. The basic ideas could also be applied to TD-OCT.

REFERENCES

The following references are hereby incorporated by reference:

Patent Documents

Ellerbee, U.S. Pat. No. 8,446,593
Ellerbee et al., US Patent Publication No. 20130215431
U.S. Pat. No. 7,391,520
U.S. Pat. No. 8,319,974
U.S. Pat. No. 8,705,048
U.S. Pat. No. 8,427,654
US Patent No. 20130100456

Non-Patent Literature

Blazkiewicz, P. et al., Appl. Opt. 44, 7722, 2005
Bonin, T. et al., Opt. Lett. 35, 3432-4, 2010
Choma, M. et al., Opt. Express 11, 2183-9, 2003
Ellerbee et al., Opt Exp 21, 26542, 2013.
Fercher, A. F. et al., Opt. Commun. 117, 43-48, 1995
Fercher, A. F. et al., Opt. Lett. 13, 186, 1988
Grajciar, B. et al., Opt. Express 13, 1131, 2005
Gronle et al., App Opt 50, 4574, 2011.
Hiratsuka, H. et al., Opt. Lett. 23, 1420
Huang, D. et al., Science 254, 1178-81, 1991
Klein, T. et al., Biomed. Opt. Express 4, 619-34, 2013
Lee, S.-W. et al., IEEE J. Sel. Topics Quantum Electron. 14, 50-55, 2008

Leitgeb, R. et al., Opt. Express 11, 889, 2003
Mohamed et al., Int J Emerg Tech & Adv Eng 2, 20, 2012.
Mujat, M. et al., Optical Coherence Tomography and Coherence Domain Optical Methods in Biomedicine XIII 7168, 71681E, 2009
Nakamura, Y. et al., Opt. Express 15, 7103, 2007
Nankivil, D. et al., Opt. Lett. 39, 3740-3, 2014
Peroz et al., Opt Lett 37, 695, 2012.
Potsaid, B. et al., Opt. Express 18, 20029-48, 2010
Považay, B. et al., Opt. Express 14, 7661, 2006
Tearney et al., Opt Lett 23, 1152, 1998.
Tearney et al., Opt Lett 27, 412, 2002.
Wieser, W. et al., Opt. Express 18, 14685-704, 2010
Wolf, E., Opt. Commun. 1, 153-156, 1969
Yelin et al., Opt Exp 15, 2432, 2007.
Yelin et al., Opt Lett 28, 2321, 2003.
Zhou et al., Opt Exp 21, 19219, 2013.
Zuluaga, A. F. et al., Opt. Lett. 24, 519-521, 1999

The invention claimed is:

1. An optical coherence tomographic system to image a sample, comprising:
    a light source for generating a beam of light, which is divided into a reference arm light and a sample arm light;
    an optical train in the sample arm containing a spectral disperser for dispersing the beam-of-light into a spectrum and laterally translating the spectrum along said sample in a direction parallel to the spread of the spectrum such that spatial points of said sample can be illuminated by at least two distinct portions of said spectrum by the translation of said spectrum with respect to the sample;
    an interferometer including a detector, for interfering back-reflected light from said spatial points with reference arm light to yield two or more partial spectrum A-scans; and
    a processor, for combining the two or more partial spectrum A-scans each obtained with distinct portions of said spectrum at a given spatial point into a combined A-scan.

2. A system as recited in claim 1 wherein the spectral disperser can be rotated.

3. A system as recited in claim 1 in which the spectral disperser is selected from the group consisting of dispersing transmission prism, dispersing reflection prism, reflection grating, transmission grating, grism, spectrally dispersing fiber or fibers, and multiband wavelength demultiplexer.

4. A system as recited in claim 1 wherein said processor converts one or more combined A-scans into an image.

5. A system as recited in claim 1 wherein the light returning from the sample is spectrally combined by the spectral disperser and delivered to an optical fiber wherein the output of the optical fiber is directed to the detector.

6. A system as recited in claim 1 wherein the detector is a spectrometer including optics to angularly disperse the beam as function of wavelength to fall on a linear array of detector elements with the position of the detector elements within the array being mapped to the illuminated spatial points on the sample.

7. A system as recited in claim 1 wherein the wavelength of the light generated by the light source is swept in time.

8. A system as recited in claim 7 wherein the detector is a photodetector with the detection time being mapped to the illuminated spatial points on the sample.

9. A method to image a patient's eye with an OCT instrument, comprising:
    dispersing a beam-of-light as a function of wavelength onto a sample to illuminate a set of spatial points, wherein each spatial point along the direction of dispersion is illuminated by a different wavelength component of the beam;
    interfering back-reflected light from the sample with a reference beam and detecting a partial spectrum A-scan at each spatial point;
    moving the spectrally dispersed beam of light along the direction of dispersion and obtaining multiple partial spectrum A-scans at each spatial point;
    processing the partial spectrum A-scans associated with individual spatial points to generate combined A-scans; and,
    displaying, storing, or further processing said combined A-scans.

10. A method as recited in claim 9 wherein the light back reflected from the eye is spectrally recombined and delivered to an optical fiber wherein the output of the optical fiber is directed a detector.

11. A method as recited in claim 10 wherein the detector is a spectrometer including optics to angularly disperse the beam as function of wavelength to fall on a linear array of detector elements with the position of the detector elements within the array being mapped to the location of particular wavelengths of radiation on the eye.

12. A method as recited in claim 9 wherein the beam of light is dispersed by an optical element selected from the group consisting of dispersing transmission prism, dispersing reflection prism, reflection grating, transmission grating, grism, spectrally dispersing fiber or fibers, and multiband wavelength demultiplexer.

13. A system as recited in claim 12 wherein the optical element is rotated.

14. A method as recited claim 9 wherein the beam of light is generated by a light source and wherein the wavelength of the light generated by the light source is swept in time.

15. An optical coherence tomography system comprising:
    a light source for generating a beam of radiation;
    a beam splitter for dividing the beam between a sample path and a reference path;
    optics, located in the sample path, for angularly dispersing the beam as a function of wavelength to create an elongated beam spot that varies in wavelength over the length of the spot, said spot being directed to illuminate the sample;
    collection optics to combine and interfere radiation returning from the sample and from the reference path;
    a spectrometer including optics to angularly disperse the beam as function of wavelength to fall on a linear array of detector elements with the position of the detector elements within the array being mapped to the location of particular wavelengths of radiation on the sample; and
    a scanner for scanning the elongated beam spot along the length axis of the beam to sequentially change the wavelength of light falling on each illuminated location on the sample wherein the multiple wavelength information collected from each illuminated location on the sample corresponds to the reflected intensity as a function of depth in the sample at that location.

16. A system as recited in claim 15 wherein the light returning from the sample is spectrally combined by the dispersing optics and delivered to an optical fiber wherein the output of the optical fiber is directed to the spectrometer.

17. A system as recited in claim 15 wherein the dispersing optics is selected from the group consisting of dispersing transmission prism, dispersing reflection prism, reflection grating, transmission grating, grism, spectrally dispersing fiber or fibers, and multiband wavelength demultiplexer.

18. A system as recited in claim 17 wherein the dispersing optics are rotated.

19. An optical coherence tomography system comprising:
- a light source for generating a beam of radiation, wherein the wavelength of the light is swept is in time;
- a beam splitter for dividing the beam between a sample path and a reference path;
- optics, located in the sample path, for angularly directing the beam as a function of wavelength so that the beam is scanned over a linear array of locations on the sample as the wavelength of the light is swept;
- collection optics to combine and interfere radiation returning from the sample and from the reference path;
- a detector for measuring the intensity of the interfered radiation, with the detection time being mapped to the location of particular wavelengths of radiation on the sample; and
- a scanner for scanning the beam in a direction parallel to the linear array of locations on the sample to sequentially change the wavelength of light falling on each illuminated location on the sample wherein the multiple wavelength information collected from each illuminated location on the sample corresponds to the reflected intensity as a function of depth in the sample at that location.

* * * * *

UNITED STATES PATENT AND TRADEMARK OFFICE
CERTIFICATE OF CORRECTION

PATENT NO. : 9,636,011 B2  
APPLICATION NO. : 14/789889  
DATED : May 2, 2017  
INVENTOR(S) : Utkarsh Sharma et al.

Page 1 of 1

It is certified that error appears in the above-identified patent and that said Letters Patent is hereby corrected as shown below:

In the Specification

In Column 8, Line 15, after "elongation" insert -- . --.

In the Claims

In Column 12, Line 35, in Claim 14, delete "recited claim" and insert -- recited in claim --, therefor.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*